United States Patent

Huitema et al.

(10) Patent No.: US 10,939,911 B2
(45) Date of Patent: Mar. 9, 2021

(54) SURGICAL STAPLER WITH END EFFECTOR COATING

(71) Applicant: Ethicon LLC, Guaynabo, PR (US)

(72) Inventors: Thomas W. Huitema, Cincinnati, OH (US); Xintian Ming, Bridgewater, NJ (US); Tamara S. Widenhouse, Clarksville, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 182 days.

(21) Appl. No.: 15/621,551

(22) Filed: Jun. 13, 2017

(65) Prior Publication Data

US 2018/0353180 A1    Dec. 13, 2018

(51) Int. Cl.
  *A61B 17/072* (2006.01)
  *A61L 31/16* (2006.01)
  *A61L 31/10* (2006.01)
  *A61L 31/14* (2006.01)
  *A61L 31/06* (2006.01)
  (Continued)

(52) U.S. Cl.
  CPC .... *A61B 17/07292* (2013.01); *A61B 17/0644* (2013.01); *A61B 17/072* (2013.01); *A61B 17/07207* (2013.01); *A61L 31/06* (2013.01); *A61L 31/10* (2013.01); *A61L 31/14* (2013.01); *A61L 31/16* (2013.01); *A61B 17/064* (2013.01); *A61B 17/1155* (2013.01); *A61B 2017/00004* (2013.01); *A61B 2017/00464* (2013.01); *A61B 2017/00477* (2013.01); *A61B 2017/00526* (2013.01); *A61B 2017/00884* (2013.01); *A61B 2017/00893* (2013.01); *A61B 2017/07257* (2013.01); *A61B 2017/07271* (2013.01); *A61B 2017/07278* (2013.01); *A61B 2017/07285* (2013.01); *A61L 2420/02* (2013.01)

(58) Field of Classification Search
  CPC .......... A61B 17/07292; A61B 17/0644; A61B 17/072; A61B 17/07207; A61L 31/06; A61L 31/10; A61L 31/14; A61L 31/16
  USPC ............... 227/19, 175.1, 176.1, 178.1, 180.1
  See application file for complete search history.

(56) References Cited

U.S. PATENT DOCUMENTS 5,684,125 A   11/1997  Nooren
6,413,539 B1   7/2002  Shalaby
(Continued)

FOREIGN PATENT DOCUMENTS

EP    3135221 A1    3/2017
EP    3135222 A1    3/2017
(Continued)

OTHER PUBLICATIONS

Agren et al., Action of matrix metalloproteinases at restricted sites in colon anastomosis repair: an immunohistochemical and biochemical study. Surgery. Jul. 2006;140(1):72-82.
(Continued)

*Primary Examiner* — Nathaniel C Chukwurah
(74) *Attorney, Agent, or Firm* — Mintz Levin Cohn Ferris Glovsky and Popeo, P.C.

(57) ABSTRACT

Methods and devices are provided for promoting wound healing. In general, surgical staplers and stapler components are provided having a coating thereon that is configured to selectively control an interaction between at least one matrix metalloproteinase (MMP) inhibitor and an outer surface of the stapler or stapler component.

13 Claims, 7 Drawing Sheets

(51) Int. Cl.
*A61B 17/064* (2006.01)
*A61B 17/00* (2006.01)
*A61B 17/115* (2006.01)

(56) References Cited

U.S. PATENT DOCUMENTS

| | | |
|---|---|---|
| 6,626,916 B1 | 9/2003 | Yeung et al. |
| 7,143,925 B2 | 12/2006 | Shelton, IV et al. |
| 7,601,118 B2 | 10/2009 | Smith et al. |
| 7,985,415 B2 | 7/2011 | Giroux |
| 8,317,070 B2 | 11/2012 | Hueil et al. |
| 8,393,514 B2 | 3/2013 | Shelton, IV et al. |
| 2002/0010482 A1 | 1/2002 | Watt |
| 2002/0025925 A1 | 2/2002 | Wood et al. |
| 2004/0219509 A1 | 11/2004 | Valkirs et al. |
| 2005/0058768 A1 | 3/2005 | Teichman |
| 2006/0025813 A1 | 2/2006 | Shelton et al. |
| 2006/0088572 A1 | 4/2006 | Tijsma et al. |
| 2006/0147492 A1 | 7/2006 | Hunter et al. |
| 2006/0235469 A1* | 10/2006 | Viola .......... A61B 17/064 606/219 |
| 2006/0270719 A1 | 11/2006 | Hayakawa et al. |
| 2007/0078413 A1 | 4/2007 | Stenzel |
| 2007/0134288 A1 | 6/2007 | Parsonage et al. |
| 2007/0225761 A1 | 9/2007 | Shetty |
| 2008/0057104 A1 | 3/2008 | Walker |
| 2008/0078807 A1 | 4/2008 | Hess et al. |
| 2008/0110961 A1 | 5/2008 | Voegele et al. |
| 2008/0124405 A1 | 5/2008 | Lin |
| 2008/0215136 A1 | 9/2008 | Gregorich et al. |
| 2008/0305143 A1 | 12/2008 | Chen et al. |
| 2009/0068255 A1 | 3/2009 | Yu et al. |
| 2009/0114701 A1 | 5/2009 | Zemlok et al. |
| 2009/0198321 A1 | 8/2009 | Sutermeister et al. |
| 2009/0239829 A1 | 9/2009 | Rossello et al. |
| 2010/0198257 A1 | 8/2010 | Stopek et al. |
| 2010/0211097 A1 | 8/2010 | Hadba et al. |
| 2010/0239635 A1 | 9/2010 | McClain et al. |
| 2011/0274732 A1 | 11/2011 | Srivastav et al. |
| 2012/0088722 A1 | 4/2012 | D'Angelo et al. |
| 2012/0241497 A1 | 9/2012 | Mandakolathur Vasudevan et al. |
| 2012/0241499 A1 | 9/2012 | Baxter, III et al. |
| 2012/0241502 A1* | 9/2012 | Aldridge .......... A61B 17/07292 227/176.1 |
| 2012/0253298 A1 | 10/2012 | Henderson et al. |
| 2013/0041406 A1 | 2/2013 | Bear et al. |
| 2013/0075447 A1 | 3/2013 | Weisenburgh, II et al. |
| 2013/0146643 A1 | 6/2013 | Schmid et al. |
| 2013/0221065 A1 | 8/2013 | Aronhalt et al. |
| 2013/0256365 A1 | 10/2013 | Shelton, IV et al. |
| 2013/0256377 A1 | 10/2013 | Schmid et al. |
| 2014/0205637 A1 | 7/2014 | Widenhouse et al. |
| 2015/0104427 A1 | 4/2015 | Segura |
| 2015/0129634 A1 | 5/2015 | Shelton, IV et al. |
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0134077 A1 | 5/2015 | Shelton, IV et al. |
| 2015/0209109 A1 | 7/2015 | Rege et al. |
| 2015/0272575 A1 | 10/2015 | Leimbach et al. |
| 2015/0283287 A1 | 10/2015 | Agarwal et al. |
| 2015/0351758 A1 | 12/2015 | Shelton, IV et al. |
| 2016/0089148 A1 | 3/2016 | Harris et al. |
| 2016/0333070 A1 | 11/2016 | Ben-Sasson et al. |
| 2017/0055984 A1 | 3/2017 | Widenhouse et al. |
| 2017/0055986 A1 | 3/2017 | Harris et al. |
| 2017/0056009 A1 | 3/2017 | Shelton, IV et al. |
| 2018/0353174 A1 | 12/2018 | Widenhouse et al. |
| 2018/0353175 A1 | 12/2018 | Widenhouse et al. |
| 2018/0353659 A1 | 12/2018 | Widenhouse et al. |
| 2019/0269403 A1 | 9/2019 | Baxter, III et al. |

FOREIGN PATENT DOCUMENTS

| | | |
|---|---|---|
| EP | 3135306 A1 | 3/2017 |
| EP | 3135307 A1 | 3/2017 |
| EP | 3135308 A1 | 3/2017 |
| EP | 3135317 A1 | 3/2017 |
| EP | 3135322 A1 | 3/2017 |
| WO | 2012/177408 A1 | 12/2012 |

OTHER PUBLICATIONS

Balbin et al., Collagenase 2 (MMP-8) expression in murine tissue remodeling processes. Analysis of its potential role in postpartum involution of the uterus. J Biol Chem. Sep. 11, 1998;273(37):23959-68.
Bosmans et al., Colorectal anastomotic healing: why the biological processes that lead to anastomotic leakage should be revealed prior to conducting intervention studies. BMC Gastroenterol. Dec. 21, 2015;15:180.
De Hingh et al., The matrix metalloproteinase inhibitor BB-94 improves the strength of intestinal anastomoses in the rat. Int J Colorectal Dis. Sep. 2002;17(5):348-54.
Fatouros et al., Influence of growth factors erythropoietin and granulocyte macrophage colony stimulating factor on mechanical strength and healing of colonic anastomoses in rats. Eur J Surg. Oct. 1999;165(10):986-92.
Hayden et al., The role of matrix metalloproteinases in intestinal epithelial wound healing during normal and inflammatory states. J Surg Res. Jun. 15, 2011;168(2):315-24.
Holte et al., Cyclo-oxygenase 2 inhibitors and the risk of anastomotic leakage after fast-track colonic surgery. Br J Surg. Jun. 2009;96(6):650-4.
Kaemmer et al., Erythropoietin (EPO) influences colonic anastomotic healing in a rat model by modulating collagen metabolism. J Surg Res. Oct. 2010;163(2):e67-72.
Kiyama et al., Tacrolimus enhances colon anastomotic healing in rats. Wound Repair Regen. Sep.-Oct. 2002;10(5):308-13.
Klein et al., Effect of diclofenac on cyclooxygenase-2 levels and early breaking strength of experimental colonic anastomoses and skin incisions. Eur Surg Res. 2011;46(1):26-31.
Krarup et al., Expression and inhibition of matrix metalloproteinase (MMP)-8, MMP-9 and MMP-12 in early colonic anastomotic repair. Int J Colorectal Dis. Aug. 2013;28(8):1151-9.
Martens et al., Postoperative changes in collagen synthesis in intestinal anastomoses of the rat: differences between small and large bowel. Gut. Dec. 1991;32(12):1482-7.
Mitchell et al., Cloning, expression, and type II collagenolytic activity of matrix metalloproteinase-13 from human osteoarthritic cartilage. J Clin Invest. Feb. 1, 1996;97(3):761-8.
Moran et al., The effect of erythropoietin on healing of obstructive vs nonobstructive left colonic anastomosis: an experimental study. World J Emerg Surg. May 15, 2007;2:13.
Oines et al., Pharmacological interventions for improved colonic anastomotic healing: a meta-analysis. World J Gastroenterol. Sep. 21, 2014;20(35):12637-48.
Raptis et al., The effects of tacrolimus on colonic anastomotic healing in rats. Int J Colorectal Dis. Mar. 2012;27(3):299-308.
Savage et al., Role of matrix metalloproteinases in healing of colonic anastomosis. Dis Colon Rectum. Aug. 1997;40(8):962-70.
Siemonsma et al., Doxycycline improves wound strength after intestinal anastomosis in the rat. Surgery. Mar. 2003;133(3):268-76.
U.S. Appl. No. 15/621,565 entitled "Surgical Fastener Device for the Prevention of ECM Degradation" filed Jun. 13, 2017.
U.S. Appl. No. 15/621,572 entitled "Surgical Stapler with Controlled Healing" filed Jun. 13, 2017.
U.S. Appl. No. 15/621,636 entitled "Surgical Fastener with Broad Spectrum MMP Inhibitors" filed Jun. 13, 2017.
Brew et al., Tissue inhibitors of metalloproteinases: evolution, structure and function. Biochim Biophys Acta. Mar. 7, 2000;1477(1-2):267-83.

(56) References Cited

OTHER PUBLICATIONS

Maskos et al., Structural basis of matrix metalloproteinases and tissue inhibitors of metalloproteinases. Mol Biotechnol. Nov. 2003;25(3):241-66.

Pasternak et al., Elevated intraperitoneal matrix metalloproteinases-8 and -9 in patients who develop anastomotic leakage after rectal cancer surgery: a pilot study. Colorectal Dis. Jul. 2010;12(7 Online):e93-8.

Sorsa et al., Matrix metalloproteinases: contribution to pathogenesis, diagnosis and treatment of periodontal inflammation. Ann Med. 2006;38(5):306-21.

Stumpf et al., Changes of the extracellular matrix as a risk factor for anastomotic leakage after large bowel surgery. Surgery. Feb. 2005;137(2):229-34.

Vandenbroucke et al., Is there new hope for therapeutic matrix metalloproteinase inhibition? Nat Rev Drug Discov. Dec. 2014;13(12):904-27.

Extended European Search Report received for European Patent Application No. 18177362.3 dated Oct. 30, 2018 (7 pages).

International Search Report and Written Opinion received for PCT International Application No. PCT/IB2018/053444 dated Aug. 29, 2018 (12 pages).

\* cited by examiner

SURGICAL STAPLER WITH END EFFECTOR COATING

FIELD

The subject matter disclosed herein relates to surgical instruments, and in particular to methods, devices, and components thereof for cutting and stapling tissue.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having a pair of movable opposed jaws formed on an end thereof for holding and forming staples therebetween. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut and/or open the stapled tissue between the stapled rows.

While surgical staplers have improved over the years, a number of problems still present themselves. One common problem is that leaks can occur due to the staple forming holes when penetrating the tissue or other object in which it is disposed. Blood, air, gastrointestinal fluids, and other fluids can seep through the openings formed by the staples, even after the staple is fully formed.

Accordingly, there remains a need for improved devices and methods for stapling tissue, blood vessels, ducts, shunts, or other objects or body parts such that leaking at the site of staple insertion is minimized.

SUMMARY

In general, surgical staplers and components thereof are provided having a coating thereon that is configured to selectively control an interaction between at least one matrix metalloproteinase (MMP) inhibitor and an outer surface of the staplers or component.

In one aspect, a staple cartridge assembly for use with a surgical stapler is provided that includes a cartridge body. The cartridge body has a plurality of staple cavities. Each staple cavity has a surgical staple disposed therein. The cartridge body also has a plurality of staple drivers, with each staple driver disposed in one of the plurality of staple cavities and which are upwardly movable to eject the plurality of staples from the plurality of staple cavities. The cartridge body further has a sled longitudinally movable through the cartridge body and configured to cause upward movement of the plurality of staple drivers. At least a portion of an outer surface of at least one of the cartridge body, the plurality of staple cavities, the plurality of staples, and the plurality of staple drivers can include a coating configured to selectively control an interaction between at least one matrix metalloproteinase (MMP) inhibitor and the outer surface.

In one embodiment, the plurality of staples can include a coating configured to permit adhesion of at least one MMP inhibitor, and at least one of the cartridge body, the plurality of staple drivers, and the sled can include a coating configured to at least minimize adhesion of an MMP inhibitor to an outer surface. The coating can be disposed on at least a portion of an outer surface of at least one of the cartridge body, the plurality of staple drivers, and the sled, and the coating can include at least one masking agent configured to at least minimize adhesion of the MMP inhibitor to the outer surface. The masking agent can be selected from the group consisting of a lubricant, parlyene, and combinations thereof. The coating can be disposed on at least a portion of the plurality of staples, and can include a substance configured to permit adhesion of the MMP inhibitor to the outer surface. The substance can be, for example, an absorbable polymer and/or an absorbable lubricant. The absorbable polymer can be, for example, polyurethane. The absorbable polymer can be polymerized in the presence of the MMP inhibitor, thereby resulting in an absorbable polymer/MMP inhibitor blend. The substance can be water soluble. The substance can absorbable and ionically charged.

In another aspect, a surgical stapling assembly is provided that in one implementation has a stapling device and a staple cartridge. The stapling device has an elongate shaft with an end effector at a distal end thereof, with the end effector having first and second jaws configured to engage tissue therebetween. The staple cartridge is configured to be disposed in one of the first and second jaws and includes a plurality of staples seated in a plurality of staple cavities. At least a portion of the plurality of staples is coated with a substance that promotes adhesion of a matrix metalloproteinase (MMP) inhibitor thereto, and at least a portion of the staple cartridge is coated with a substance that inhibits adhesion of an MMP inhibitor thereto. The assembly can optionally include an adjunct configured to be disposed on at least one of the first and second jaws. The adjunct can include an effective amount of at least one MMP inhibitor disposed within and releasable from the adjunct material. The MMP inhibitor can be releasably retained on the plurality of staples and it can be configured to be delivered to tissue by deployment of the staples in the cartridge body.

In a further aspect, provided herein is a method for manufacturing a staple cartridge assembly for use with a surgical stapler. In one embodiment, the method can include applying a first coating configured to inhibit adhesion of a matrix metalloproteinase (MMP) inhibitor to at least a portion of at least one of a cartridge body having a plurality of staple cavities, a plurality of staple drivers, and a sled slidably movable through the cartridge body. The method can also include applying a second coating configured to promote adhesion of an MMP inhibitor to at least a portion of a plurality of staples. The method can further include loading the plurality of staples into the plurality of staple cavities.

In one embodiment, the second coating can be applied to at least one of a first leg, a second leg, and a crown of the plurality of staples. The first coating can be applied to the plurality of staple cavities. The second coating can be applied using various techniques, such as vapor disposition, or by dipping the plurality of staples into a substance containing the MMP inhibitor. In certain aspects, the staples can be loaded into the plurality of staple cavities prior to applying the second coating.

BRIEF DESCRIPTION OF DRAWINGS

This invention will be more fully understood from the following detailed description taken in conjunction with the accompanying drawings, in which.

DETAILED DESCRIPTION

Figure 1:
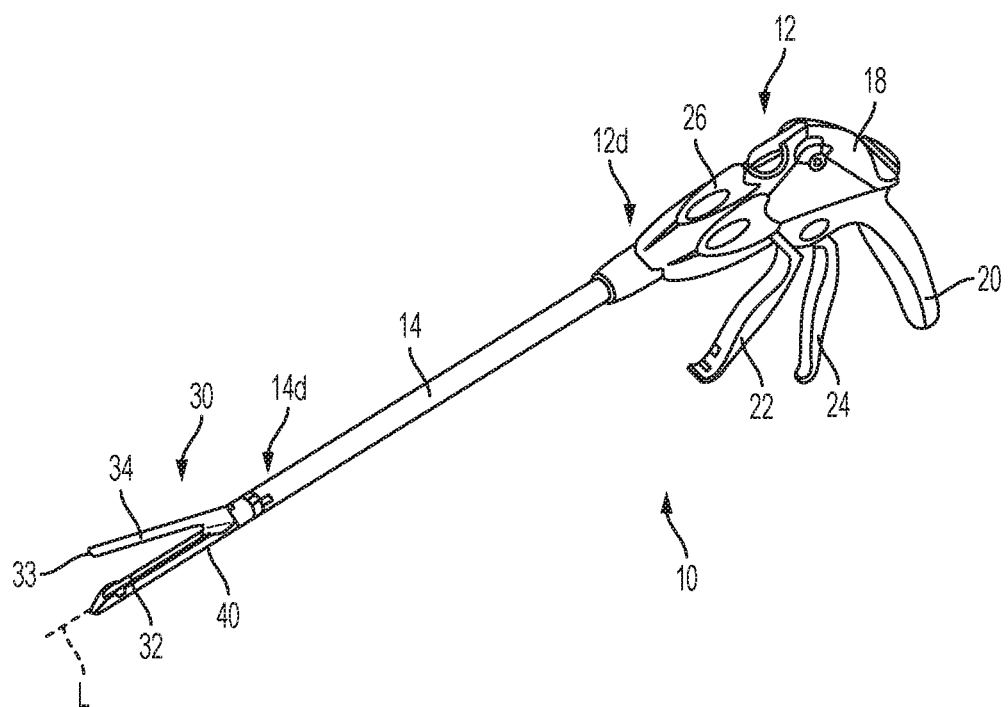
FIG. 1 is a perspective view of one embodiment of a surgical stapler.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Various exemplary devices and methods are provided for performing surgical procedures. In some embodiments, the devices and methods are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

During performance of a surgical procedure, tissue of a patient can be wounded (e.g., cut, torn, punctured, etc.) in any of a variety of ways. The wounding may be an intended aspect of the surgical procedure, such as in an anastomosis procedure and/or when tissue is cut and fastened using a surgical device such as a surgical stapler. The wounded tissue typically heals over time in generally the same way for all patients.

Wound healing is traditionally considered to include four stages: hemostasis, inflammation, proliferation, and remodeling. The hemostasis stage generally involves blood clotting, e.g., stopping bleeding. In general, damaged blood vessels constrict to slow blood flow, platelets aggregate to help seal the wound site, the platelets activate fibrin to further facilitate wound sealing, and a blood clot forms at the wound site. The inflammation stage generally involves cleaning of the wound site. In general, the immune system provides a response to the threat of possible infection at the wound site via signaling to defensive immune cells such as neutrophils and macrophages. The proliferation stage generally involves rebuilding tissue with tissue growth and angiogenesis (blood vessel growth). In general, fibroblasts arrive at the wound site, lay down collagen, release growth factors that attract epithelial cells, and the epithelial cells attract endothelial cells. The remodeling stage, also referred to as a maturation stage, generally involves strengthening scar tissue at the wound site. In general, collagen fibers align and crosslink, and the scar matures to eventually fade away.

While each of the four stages of wound healing involves a different aspect of the healing process, stages typically overlap with one another. Namely, each of the last three stages typically overlaps with its preceding stage, e.g., inflammation overlaps with hemostasis, proliferation overlaps with inflammation, and remodeling overlaps with proliferation. The speed at which the transition between stages occurs generally affects the speed of overall wound healing and thus generally affects patient recovery time, chances of complications arising, and/or patient comfort. Similarly, the length of each of the four individual stages generally affects the speed of overall wound healing and the patient's general recovery.

Matrix metalloproteinases (MMPs) are a family of proteases that breakdown components of the extracellular matrix (ECM) of tissue under a variety of physiological and pathological conditions, including during wound healing. These enzymes remove dead and devitalized tissue, help to remodel the underlying connective tissue of the ECM, promote inflammatory cell migration into the wound site, and assist in angiogenesis. During the inflammation stage of wound healing, MMPs break down damaged ECM located at the edges of wounds. This enables new ECM molecules (such as, for example, collagen, elastin, and fibronectin) synthesized by cells located at or attracted to the wound site during the later stages of wound healing to eventually merge into and become part of the intact ECM, thereby resulting in wound closure and healing.

Accordingly, immediately following tissue stapling, cells present at the site of staple insertion release MMPs, which begin the process of degrading the ECM at and near the wound caused by the staple in order to facilitate the initial stages of wound healing. However, without being bound to theory, it is believed that this natural process can, at least initially, result in the weakening of tissue surrounding the staple site, making it susceptible to tearing and other complications (such as, leaking of blood, air, and other fluids through the openings formed by the staples as well as, e.g., anastomotic leakage following bowel resection). As such, and again without being bound to theory, it is believed that delivering substances capable of inhibiting MMPs to wound sites in tissue (for example, intestinal tissue) immediately after staple insertion can prevent or minimize the ECM degeneration associated with the initial stages of wound healing, thereby strengthening the staple insertion site and making it less likely to leak or rupture.

Thus, it can be desirable to use one or more MMP inhibitors, in conjunction with surgical instruments, such as surgical staplers, to help improve surgical procedures. MMP inhibitors are molecules capable of inhibiting or decreasing the proteolytic activity of MMPs on ECM components at a wound site. Without being bound to theory, by preventing the natural MMP-mediated ECM degradation that occurs immediately following staple insertion, MMP inhibitors may be able to prevent the tissue leakage complications associated with tissue stapling by strengthening the tissue surrounding the wound site. In some instances, the MMP inhibitors delivered to sites of tissue stapling as provided herein may increase the incidence of scar tissue formation leading to the minimization of tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting tissue movement around these puncture sites by preventing MMP-mediated degradation of the ECM (for example, MMP-mediated proteolysis of collagen) can encourage scar tissue formation and thereby minimize the size the holes may grow to under tension, as well as the potential for leakage.

Unfortunately, many MMP-inhibitors have physical properties, such as excessive stickiness, that prevent them from being used directly in a device containing multiple moving parts, such as a surgical stapler. As will be described in more detail herein, the present inventors have discovered that various parts of a surgical stapler and associated components can be coated with substances to facilitate MMP inhibitor deposition on one or more parts of a staple (such as the distal legs or crown) or, alternatively, to prevent MMP inhibitor deposition on other parts of the surgical staple apparatus (such as one or more movable parts or portions of the apparatus that come in contact with movable parts). These coatings prevent the malfunctioning of the surgical stapler that would otherwise be caused due to MMP inhibitor deposition on the moving parts of the stapler apparatus. Thus, following successful staple deployment, the staples can release the MMP inhibitor to the surrounding stapled tissue to strengthen the site of staple insertion and minimize the likelihood of complications associated with tissue stapling.

Surgical Stapling Instruments

A variety of surgical instruments can be used in conjunction with the medicant(s) disclosed herein. The surgical instruments can include surgical staplers. A variety of surgical staplers can be used, for example linear surgical staplers and circular staplers. In general, a linear stapler can be configured to create longitudinal staple lines and can include elongate jaws with a cartridge coupled thereto containing longitudinal staple rows. The elongate jaws can include a knife or other cutting element capable of creating a cut between the staple rows along tissue held within the jaws. In general, a circular stapler can be configured to create annular staple lines and can include circular jaws with a cartridge containing annular staple rows. The circular jaws can include a knife or other cutting element capable of creating a cut inside of the rows of staples to define an opening through tissue held within the jaws. The staplers can be used in a variety of different surgical procedures on a variety of tissues in a variety of different surgical procedures, for example in thoracic surgery or in gastric surgery.

FIG. 1 illustrates one example of a linear surgical stapler 10 suitable for use with one or more adjunct(s) and/or medicant(s) (such as an MMP inhibitor). The stapler 10 generally includes a handle assembly 12, a shaft 14 extending distally from a distal end 12d of the handle assembly 12, and an end effector 30 at a distal end 14d of the shaft 14. The end effector 30 has opposed lower and upper jaws 32, 34, although other types of end effectors can be used with the shaft 14, handle assembly 12, and components associated with the same. The lower jaw 32 has a staple channel 56 configured to support a staple cartridge 40, and the upper jaw 34 has an anvil surface 33 that faces the lower jaw 32 and that is configured to operate as an anvil to help deploy staples of the staple cartridge 40 (the staples are obscured in FIG. 1 and FIG. 2). At least one of the opposed lower and upper jaws 32, 34 is moveable relative to the other lower and upper jaws 32, 34 to clamp tissue and/or other objects disposed therebetween. In some implementations, one of the opposed lower and upper jaws 32, 34 may be fixed or otherwise immovable. In some implementations, both of the opposed lower and upper jaws 32, 34 may be movable. Components of a firing system can be configured to pass through at least a portion of the end effector 30 to eject the staples into the clamped tissue. In various implementations a knife blade 36 or other cutting element can be associated with the firing system to cut tissue during the stapling procedure.

Operation of the end effector 30 can begin with input from a user, e.g., a clinician, a surgeon, etc., at the handle assembly 12. The handle assembly 12 can have many different configurations designed to manipulate and operate the end effector 30 associated therewith. In the illustrated example, the handle assembly 12 has a pistol-grip type housing 18 with a variety of mechanical and/or electrical components disposed therein to operate various features of the instrument 10. For example, the handle assembly 12 can include a rotation knob 26 mounted adjacent a distal end 12d thereof which can facilitate rotation of the shaft 14 and/or the end effector 30 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 32, 34 to collapse towards each other and to thereby clamp tissue therebetween. Movement of the firing trigger 24 can actuate the firing system, described below, which can cause the ejection of staples from the staple cartridge 40 disposed therein and/or the advancement the knife blade 36 to sever tissue captured between the jaws 32, 34. A person skilled in the art will recognize that various configurations of components for a firing system, mechanical, hydraulic, pneumatic, electromechanical, robotic, or otherwise, can be used to eject staples and/or cut tissue.

Figure 2:
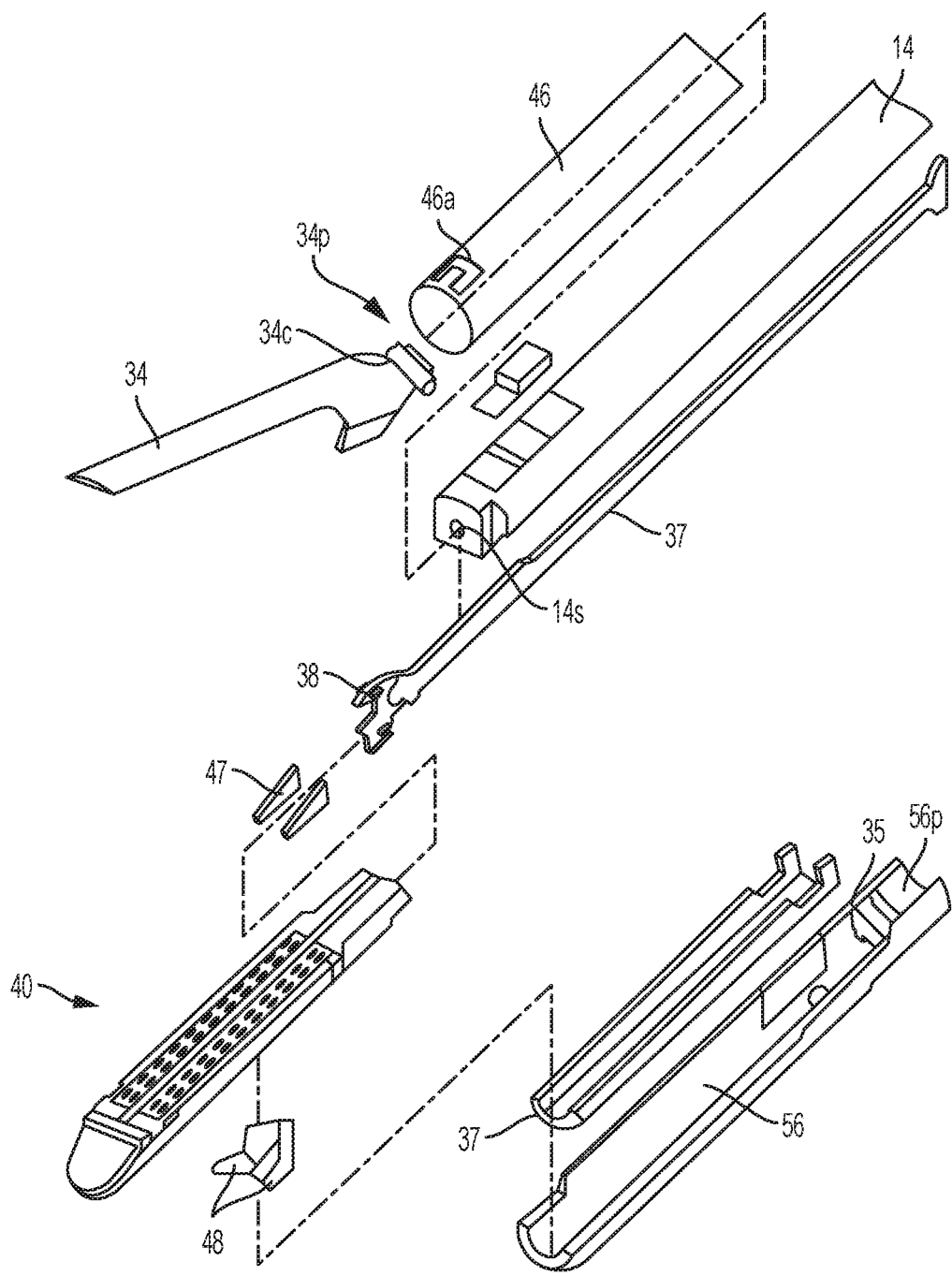
FIG. 2 is an exploded view of a distal portion of the surgical stapler of FIG. 1.

As shown in FIG. 1 and FIG. 2, the end effector 30 of the illustrated implementation has the lower jaw 32 that serves as a cartridge assembly or carrier and the opposed upper jaw 34 that serves as an anvil. The staple cartridge 40, having a plurality of staples therein, is supported in a staple tray 37, which in turn is supported within a cartridge channel of the lower jaw 32. The upper jaw 34 has a plurality of staple forming pockets (not shown), each of which is positioned above a corresponding staple from the plurality of staples contained within the staple cartridge 40. The upper jaw 34 can be connected to the lower jaw 32 in a variety of ways, although in the illustrated implementation the upper jaw 34 has a proximal pivoting end 34p that is pivotally received within a proximal end 56p of the staple channel 56, just distal to its engagement to the shaft 14. When the upper jaw 34 is pivoted downwardly, the upper jaw 34 moves the anvil surface 33 and the staple forming pockets formed thereon move toward the opposing staple cartridge 40.

Various clamping components can be used to effect opening and closing of the jaws 32, 34 to selectively clamp tissue therebetween. As illustrated, the pivoting end 34p of the upper jaw 34 includes a closure feature 34c distal to its pivotal attachment with the staple channel 56. Thus, a closure tube 46, whose distal end includes a horseshoe aperture 46a that engages the closure feature 34c, selectively imparts an opening motion to the upper jaw 34 during proximal longitudinal motion and a closing motion to the upper jaw 34 during distal longitudinal motion of the closure tube 46 in response to the clamping trigger 22. As mentioned above, in various implementations, the opening and closure of the end effector 30 may be effected by relative motion of the lower jaw 32 with respect to the upper jaw 34, relative motion of the upper jaw 34 with respect to the lower jaw 32, or by motion of both jaws 32, 34 with respect to one another.

Figure 3:
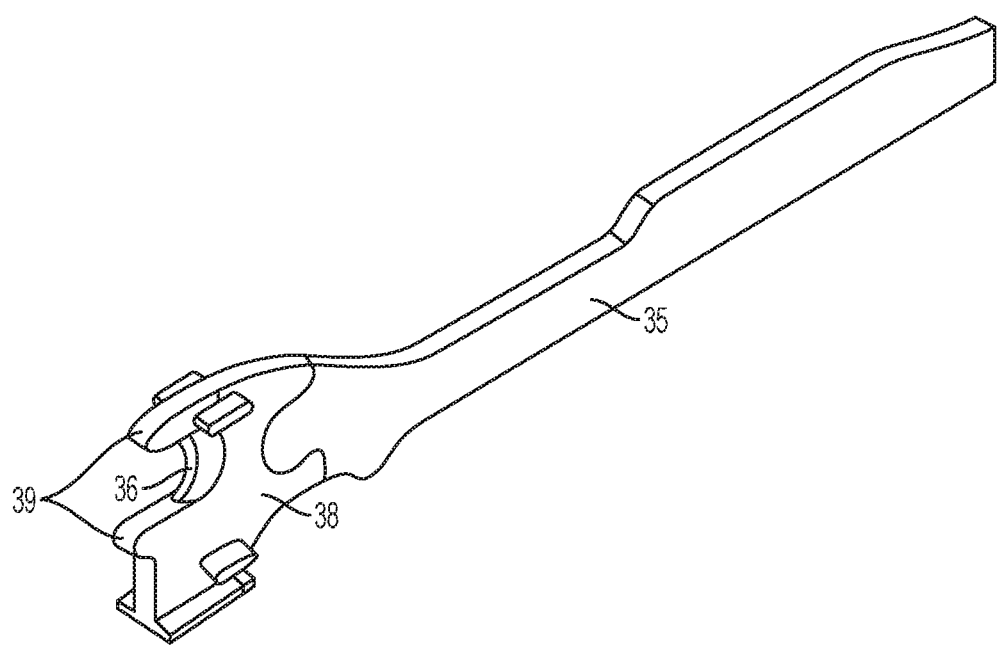
FIG. 3 is a perspective view of a firing bar of the surgical stapler of FIG. 1, the firing bar having an E-beam at a distal end thereof.

The firing components of the illustrated implementation includes a firing bar 35, as shown in FIG. 3, having an E-beam 38 on a distal end thereof. The firing bar 35 is encompassed within the shaft 14, for example in a longitudinal firing bar slot 14s of the shaft 14, and guided by a firing motion from the handle 12. Actuation of the firing trigger 24 can affect distal motion of the E-beam 38 through at least a portion of the end effector 30 to thereby cause the firing of staples contained within the staple cartridge 40. As illustrated, guides 39 projecting from a distal end of the E-Beam 38 can engage a wedge sled 47 shown in FIG. 2, which in turn can push staple drivers 48 upwardly through staple cavities 41 formed in the staple cartridge 40. Upward movement of the staple drivers 48 applies an upward force on each of the plurality of staples within the cartridge 40 to thereby push the staples upwardly against the anvil surface 33 of the upper jaw 34 and create formed staples.

In addition to causing the firing of staples, the E-beam 38 can be configured to facilitate closure of the jaws 32, 34, spacing of the upper jaw 34 from the staple cartridge 40, and/or severing of tissue captured between the jaws 32, 34. In particular, a pair of top pins and a pair of bottom pins can engage one or both of the upper and lower jaws 32, 34 to compress the jaws 32, 34 toward one another as the firing bar 35 advances through the end effector 30. Simultaneously, the knife 36 extending between the top and bottom pins can be configured to sever tissue captured between the jaws 32, 34.

In use, the surgical stapler 10 can be disposed in a cannula or port and disposed at a surgical site. A tissue to be cut and stapled can be placed between the jaws 32, 34 of the surgical stapler 10. Features of the stapler 10 can be maneuvered as desired by the user to achieve a desired location of the jaws 32,34 at the surgical site and the tissue with respect to the jaws 32, 34. After appropriate positioning has been achieved, the clamping trigger 22 can be pulled toward the stationary handle 20 to actuate the clamping system. The trigger 22 can cause components of the clamping system to operate such that the closure tube 46 advances distally through at least a portion of the shaft 14 to cause at least one of the jaws 32, 34 to collapse towards the other to clamp the tissue disposed therebetween. Thereafter, the trigger 24 can be pulled toward the stationary handle 20 to cause components of the firing system to operate such that the firing bar 35 and/or the E-beam 38 are advanced distally through at least a portion of the end effector 30 to effect the firing of staples and optionally to sever the tissue captured between the jaws 32, 34.

Figure 4:
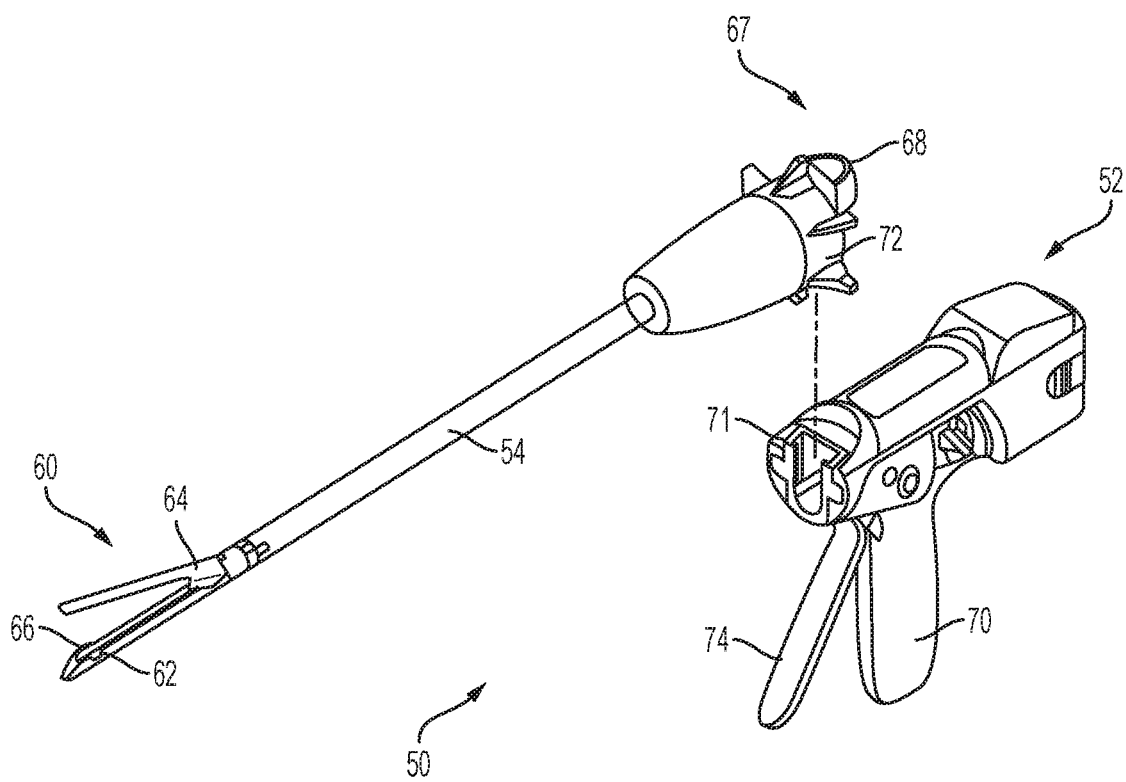
FIG. 4 is a perspective view of another embodiment of a surgical stapler.

Another example of a surgical instrument in the form of a linear surgical stapler 50 is illustrated in FIG. 4. The stapler 50 can generally be configured and used similar to the stapler 10 of FIG. 1. Similar to the surgical instrument 10 of FIG. 1, the surgical instrument 50 includes a handle assembly 52 with a shaft 54 extending distally therefrom and having an end effector 60 on a distal end thereof for treating tissue. Upper and lower jaws 64, 62 of the end effector 60 can be configured to capture tissue therebetween, staple the tissue by firing of staples from a cartridge 66 disposed in the lower jaw 62, and/or to create an incision in the tissue. In this implementation, an attachment portion 67 on a proximal end of the shaft 54 can be configured to allow for removable attachment of the shaft 54 and the end effector 60 to the handle assembly 52. In particular, mating features 68 of the attachment portion 67 can mate to complementary mating features 71 of the handle assembly 52. The mating features 68, 71 can be configured to couple together via, e.g., a snap fit coupling, a bayonet type coupling, etc., although any number of complementary mating features and any type of coupling can be used to removably couple the shaft 54 to the handle assembly 52. Although the entire shaft 54 of the illustrated implementation is configured to be detachable from the handle assembly 52, in some implementations, the attachment portion 67 can be configured to allow for detachment of only a distal portion of the shaft 54. Detachable coupling of the shaft 54 and/or the end effector 60 can allow for selective attachment of a desired end effector 60 for a particular procedure, and/or for reuse of the handle assembly 52 for multiple different procedures.

The handle assembly 52 can have one or more features thereon to manipulate and operate the end effector 60. By way of non-limiting example, a rotation knob 72 mounted on a distal end of the handle assembly 52 can facilitate rotation of the shaft 54 and/or the end effector 60 with respect to the handle assembly 52. The handle assembly 52 can include clamping components as part of a clamping system actuated by a movable trigger 74 and firing components as part of a firing system that can also be actuated by the trigger 74. Thus, in some implementations, movement of the trigger 74 toward a stationary handle 70 through a first range of motion can actuate clamping components to cause the opposed jaws 62, 64 to approximate toward one another to a closed position. In some implementations, only one of the opposed jaws 62, 24 can move to the jaws 62, 64 to the closed position. Further movement of the trigger 74 toward the stationary handle 70 through a second range of motion can actuate firing components to cause the ejection of the staples from the staple cartridge 66 and/or the advancement of a knife or other cutting element (not shown) to sever tissue captured between the jaws 62, 64.

Figure 5:
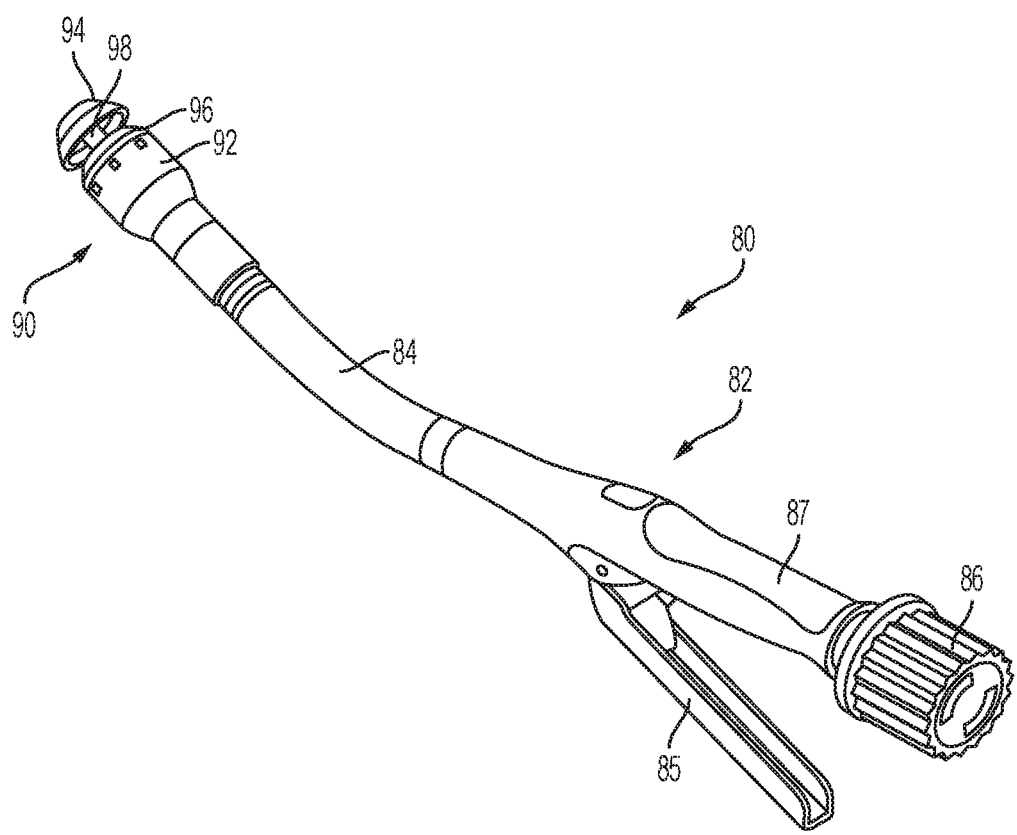
FIG. 5 is a perspective view of yet another embodiment of a surgical stapler.

One example of a surgical instrument in the form of a circular surgical stapler 80 is illustrated in FIG. 5. The stapler 80 can generally be configured and used similar to the linear staplers 10, 50 of FIG. 1 and FIG. 4, but with some features accommodating its functionality as a circular stapler. Similar to the surgical instruments 10, 50, the surgical instrument 80 includes a handle assembly 82 with a shaft 84 extending distally therefrom and having an end effector 90 on a distal end thereof for treating tissue. The end effector 90 can include a cartridge assembly 92 and an anvil 94, each having a tissue-contacting surface that is substantially circular in shape. The cartridge assembly 92 and the anvil 94 can be coupled together via a shaft 98 extending from the anvil 94 to the handle assembly 82 of the stapler 80, and manipulating an actuator 85 on the handle assembly 82 can retract and advance the shaft 98 to move the anvil 94 relative to the cartridge assembly 92. The anvil 94 and cartridge assembly 92 can perform various functions and can be configured to capture tissue therebetween, staple the tissue by firing of staples from a cartridge 96 of the cartridge assembly 92 and/or can create an incision in the tissue. In general, the cartridge assembly 92 can house a cartridge containing the staples and can deploy staples against the anvil 94 to form a circular pattern of staples, e.g., staple around a circumference of a tubular body organ.

In one implementation, the shaft 98 can be formed of first and second portions (not shown) configured to releasably couple together to allow the anvil 94 to be detached from the cartridge assembly 92, which may allow greater flexibility in positioning the anvil 94 and the cartridge assembly 92 in a body of a patient. For example, the first portion of the shaft can be disposed within the cartridge assembly 92 and extend distally outside of the cartridge assembly 92, terminating in a distal mating feature. The second portion of the shaft 84 can be disposed within the anvil 94 and extend proximally outside of the cartridge assembly 92, terminating in a proximal mating feature. In use, the proximal and distal mating features can be coupled together to allow the anvil 94 and cartridge assembly 92 to move relative to one another.

The handle assembly 82 of the stapler 80 can have various actuators disposed thereon that can control movement of the stapler. For example, the handle assembly 82 can have a rotation knob 86 disposed thereon to facilitate positioning of the end effector 90 via rotation, and/or the trigger 85 for actuation of the end effector 90. Movement of the trigger 85 toward a stationary handle 87 through a first range of motion can actuate components of a clamping system to approximate the jaws, i.e. move the anvil 94 toward the cartridge assembly 92. Movement of the trigger 85 toward the stationary handle 87 through a second range of motion can actuate components of a firing system to cause the staples to deploy from the staple cartridge assembly 92 and/or cause advancement of a knife to sever tissue captured between the cartridge assembly 92 and the anvil 94.

Various forms of implantable staple cartridges may be employed with the various embodiments of surgical instruments and instrument components disclosed herein. Specific staple cartridge configurations and constructions will be discussed in further detail below by way of non-limiting example only.

Figure 6:
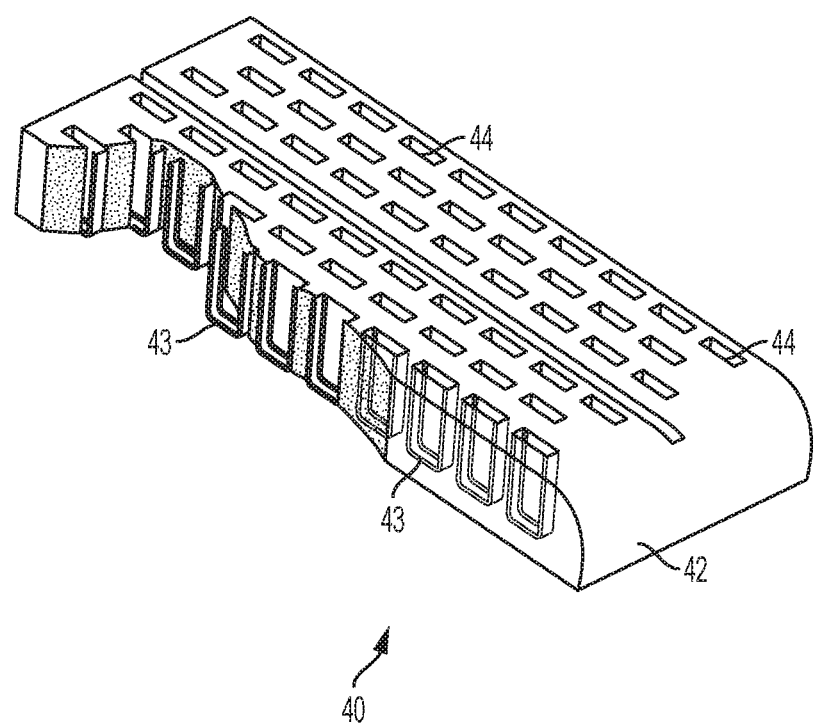
FIG. 6 is a perspective, partially cut-away view of one embodiment of an implantable staple cartridge.

In the embodiment depicted in FIG. 6, an implantable staple cartridge 40 is shown. The staple cartridge 40 has a body portion 42 that is formed from a compressible hemostat material such as, for example, oxidized regenerated cellulose ("ORC") or a bio-absorbable foam in which lines of unformed metal staples 43 are supported. The body 42 of the staple cartridge 40 is sized to be removably supported within the elongated channel 56 shown in FIG. 2 such that each staple 43 therein is aligned with corresponding staple forming pockets 44 in the anvil when the anvil 94 is driven into forming contact with the staple cartridge 40.

Figure 7:
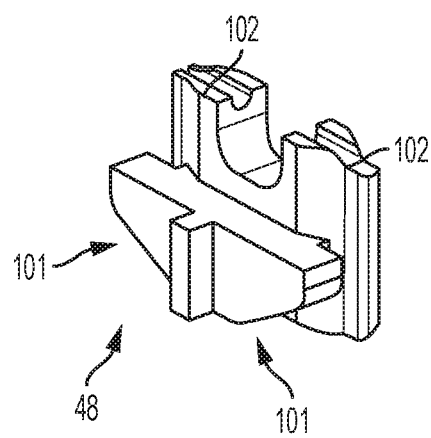
FIG. 7 is a perspective view of one embodiment of a staple driver.
Figure 8:
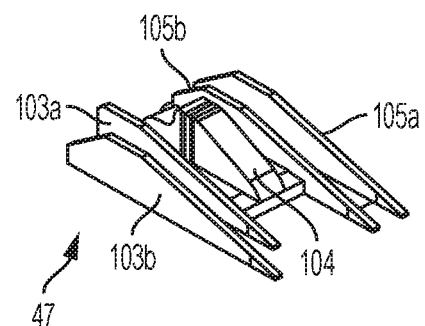
FIG. 8 is a perspective view of one embodiment of a sled.

FIG. 7 and FIG. 8 show representative embodiments of a staple driver 48 and sled 47, respectively, that may be employed with the various embodiments of the surgical instruments disclosed herein. The staple driver 48 of FIG. 7 is configured to sit within a staple pocket in the cartridge beneath a staple, and to be advanced upward as the sled of FIG. 8 translates distally through the cartridge. Each staple pocket has a staple driver 48 therein for driving the staple from the cartridge toward the anvil surface 33 as shown in FIG. 1.

Figure 9:
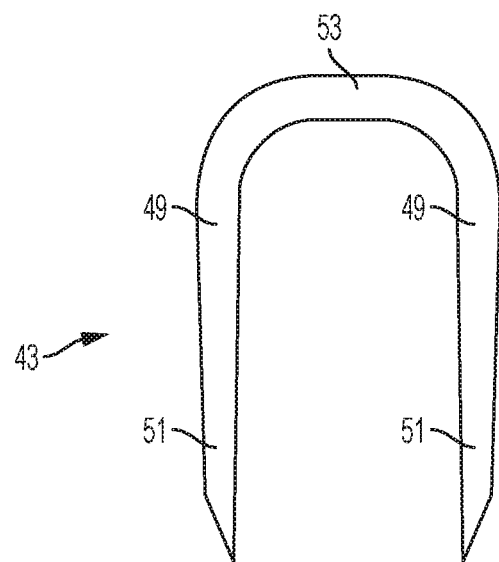
FIG. 9 is a perspective view of one embodiment of a staple.

FIG. 9 shows a representative embodiment of a staple 43 may be employed with the various embodiments of the surgical instruments disclosed herein. The staple 43 has staple legs 49, each having distal tips 51, as well as a crown 53 connecting the legs 49.

The illustrated examples of surgical stapling instruments 10, 50, and 80 provide only a few examples of many different configurations, and associated methods of use, that can be used in conjunction with the disclosures provided herein. Although the illustrated examples are all configured for use in minimally invasive procedures, it will be appreciated that instruments configured for use in open surgical procedures, e.g., open linear staplers as described in U.S. Pat. No. 8,317,070 entitled "Surgical Stapling Devices That Produce Formed Staples Having Different Lengths" and filed Feb. 28, 2007, can be used in conjunction with the disclosures provided herein. Greater detail on the illustrated examples, as well as additional examples of surgical staplers, components thereof, and their related methods of use, are provided in U.S. Pat. Pub. No. 2013/0256377 entitled "Layer Comprising Deployable Attachment Members" and filed Feb. 8, 2013, U.S. Pat. No. 8,393,514 entitled "Selectively Orientable Implantable Fastener Cartridge" and filed Sep. 30, 2010, U.S. Pat. No. 8,317,070 entitled "Surgical Stapling Devices That Produce Formed Staples Having Different Lengths" and filed Feb. 28, 2007, U.S. Pat. No. 7,143,925 entitled "Surgical Instrument Incorporating EAP Blocking Lockout Mechanism" and filed Jun. 21, 2005, U.S. Pat. Pub. No. 2015/0134077 entitled "Sealing Materials For Use In Surgical Stapling" and filed Nov. 8, 2013, entitled "Sealing Materials for Use in Surgical Procedures, and filed on Nov. 8, 2013, U.S. Pat. Pub. No. 2015/0134076, entitled "Hybrid Adjunct Materials for Use in Surgical Stapling," and filed on Nov. 8, 2013, U.S. Pat. Pub. No. 2015/0133996, entitled "Positively Charged Implantable Materials and Method of Forming the Same," and filed on Nov. 8, 2013, U.S. Pat. Pub. No. 2015/0129634, entitled "Tissue Ingrowth Materials and Method of Using the Same," and filed on Nov. 8, 2013, U.S. Pat. Pub. No. 2015/0133995, entitled "Hybrid Adjunct Materials for Use in Surgical Stapling," and filed on Nov. 8, 2013, U.S. patent application Ser. No. 14/226,142, entitled "Surgical Instrument Comprising a Sensor System," and filed on Mar. 26, 2014, and U.S. patent application Ser. No. 14/300,954, entitled "Adjunct Materials and Methods of Using Same in Surgical Methods for Tissue Sealing," and filed on Jun. 10, 2014, which are hereby incorporated by reference herein in their entireties.

MMP Inhibitors

MMPs, which comprise a family of more than 20 members, use $Zn^{2+}$ in their active sites to catalyze hydrolyses of ECM components such as collagen. Based on their substrate specificities, they can be broadly classified into three subfamilies: collagenases, stromelysins and gelatinases.

Under normal physiological conditions, these enzymes serve many important functions, including wound healing and tissue remodeling. However, when these enzymes are over activated, they can over-degrade ECM, resulting in disease conditions. For example, MMP-2 and MMP-9 (both are gelatinases) are thought to be involved in the pathogenesis of inflammatory, infectious, and neoplastic diseases in many organs. Excess activity of MMP-8, also known as collagenase-2 or neutrophil collagenase, is associated with diseases such as pulmonary emphysema and osteoarthritis. See Balbin et al., "Collagenase 2 (MMP-8) expression in murine tissue-remodeling processes, analysis of its potential role in postpartum involution of the uterus," *J. Biol. Chem.*, 273 (37): 23959-23968 (1998). Excess activity of MMP-12, also known as macrophage elastase or metalloelastase, plays a key role in tumor invasion, arthritis, atherosclerosis, Alport syndrome, and chronic obstructive pulmonary disease (COPD). MMP-1 and MMP-13 are involved in the proteolysis of collagen. Excessive degradation of collagen is associated with the development of various diseases, including osteoarthritis. See e.g., P. G. Mitchell et al., "Cloning, expression, and type II collagenolytic activity of matrix metalloproteinase-13 from human osteoarthritic cartilage," *J Clin invest.* 1996 Feb. 1; 97 (3): 761-768.

A "matrix metalloproteinase inhibitor" or "MMP inhibitor," as used herein, is any chemical compound that inhibits by at least five percent the proteolytic activity (such as inhibits any of 5%, 10%, 15%, 20%, 25%, 30%, 35%, 40%, 45%, 50%, 55%, 60%, 65%, 70%, 75%, 80%, 85%, 90%, 95%, or 100% of the proteolytic activity) of at least one matrix metalloproteinase enzyme that is naturally occurring in a mammal (such as an MMP that naturally is expressed during wound healing). Many MMP inhibitors are known in the art. For example, existing MMP inhibitors can be based on hydroxamic acid derivatives, suflonyl amino acid, and sulfonylamino hydroxamic acid derivatives. The hydroxamic acid moiety in these inhibitors binds to the MMP active site $Zn^{2+}$ to inhibit enzymatic activities. Further, numerous peptides are known matrix metalloproteinase inhibitors.

Non-limiting specific examples of matrix metalloproteinase inhibitors that inhibit or decrease the proteolytic activity of MMPs include, without limitation, exogenous MMP inhibitors, Batimastat (BB-94), Ilomastat (GM6001), Marimastat (BB2516), Thiols, Doxycycline, Squaric Acid, BB-1101, CGS-27023-A (MMI270B), COL-3 (metastat; CMT-3), Hydroxyureas, AZD3342, Hydrazines, Endogenous, Carbamoylphosphates, Beta Lactams, tetracycline and analogs and homologs of tetracycline, minocycline, 3-(4-phenoxyphenylsulfonyl)propylthiirane, pyrimidine-2,4-dione, BAY12-9566, prinomastat (AG-3340), N-{1S-[4-(4-Chlorophenyl)piperazine-1-sulfonylmethyl]-2-methylpropyl}-N-hydroxyformamide, RO 31-9790, 3-(4-PhenoxyphenylsulfonyDpropylthiirane, 1,6-bis[N'-(p-chlorophenyl)-N5-biguanido]hexane, trocade, sodium 1-(12-hydroxy)octadecanyl sulfate, minocycline (7-dimethylamino-6-dimethyl-6-deoxytetracycline), tetrapeptidylhydroxamic acid, N-[(2R)-2-(Carboxymethyl)-4-methylpentanoyl]-L-tryptophan-(S)-methyl-benzylamide, N-[(2R)-2-(Hydroxamidocarbonylmethyl)-4-methylpentanoyl]-L-tryptophan Methylamide, N-Hydroxy-1,3-di-(4-methoxybenzenesulphonyl)-5,5-dimethyl-[1,3]-piperazine-2-carboxamide, N-{1S-[4-(4-Chlorophenyl)piperazine-1-sulfonylmethyl]-2-methylpropyl}-N-hydroxyformamide, triaryl-oxy-aryloxy-pyrimidine-2,4,6-trione, 4rbiarylbutyric acid, 5-biarylpentanoic acid, Fenbufen, peptide MMPIs, hydroxamic acid, tricyclic butyric acid, biphenyl butyric acid, heterocyclic substituted phenyl v butyric acid, sulfonamide, succinamide, FN-439 (p-aminobenzoyl-Gly-Pro-D-Leu-D-Ala-NHOH, MMP-Inh-1), sulfonated amino acid, MMP9 inhibitor I (CTK8G1150), ONO-4817, SB-3CT, neutralizing anti-MMP antibody, MMI-166, tanomastat, cipemastat, MMI-270, ABT-770, prinomastat, tetrahydropyran, RS-130830, 239796-97-5, Ro-28-2653, and tacrolimus (FK506).

MMP inhibitors also include the family of tissue inhibitors of MMPs (TIMPs)). The term "TIMP," as used herein, means an endogenous tissue inhibitor of metalloproteinases, which is known to be involved in physiological/biological functions including the inhibition of active matrix metalloproteinases, regulation of pro-MMP activation, cell growth, and the modulation of angiogenesis. The human "TIMP family" contains four members, TIMP-1, TIMP-2, TIMP-3, and TIMP-4. The TIMP-1 protein is the most widely expressed and studied member of the TIMP family. Other members of the TIMP family include TIMP-2, TIMP-3 and TIMP-4. TIMP proteins not only share common structural features, including a series of conserved cysteine residues that form disulfide bonds essential for the native protein conformation (Brew et al., 2000), but they also have widely overlapping biological activities. The conserved N-terminal region of the TIMP proteins is necessary for functional inhibitory activities, while the divergent C-terminal regions are thought to modulate the selectivity of inhibition and binding efficiency of agents to the MMPs (Maskos & Bode, 2003). However, apart from their ability to act as MMP inhibitors, the various TIMP family members may also exhibit additional biological activities, including the regulation of proliferation and apoptosis in addition to the modulation of angiogenic and inflammatory responses.

TIMP-1 has been found to inhibit most MMPs (except MMP-2 and -14), and preferentially inhibits MMP-8. TIMP-1 is produced and secreted in soluble form by a variety of cell types and is widely distributed throughout the body. It is an extensively glycosylated protein with a molecular mass of 28.5 kDa. TIMP-1 inhibits the active forms of MMPs, and complexes with the proform of MMP9. Like MMP9, TIMP-1 expression is sensitive to many factors. Increased synthesis of TIMP-1 is caused by a wide variety of reagents that include: TGF beta, EGF, PDGF, FGFb, PMA, alltransretinoic acid (RA), IL1 and IL11.

TIMP-2 is a 21 kDa glycoprotein that is expressed by a variety of cell types. It forms a non-covalent, stoichiometric complex with both latent and active MMPs. TIMP-2 shows a preference for inhibition of MMP-2.

TIMP-3 is typically bound to the ECM and inhibits the activity of MMP-1, -2, -3, -9, and 13. TIMP-3 shows 30% amino acid homology with TIMP-1 and 38% homology with TIMP-2. TIMP-3 has been shown to promote the detachment of transformed cells from ECM and to accelerate morphological changes associated with cell transformation.

Due to its high-affinity binding to the ECM, TIMP-3 is unique among the TIMPs. TIMP-3 has been shown to promote the detachment of transformed cells from the ECM and to accelerate the morphological changes associated with cell transformation. TIMP-3 contains a glucosaminoglycan (GAG) binding domain comprising six amino acids (Lys30, Lys26, Lys22, Lys42, Arg20, Lys45) that are thought to be responsible for an association with the cell surface. TIMP-3 is the only TIMP that normally inhibits TACE (TNF-α-converting enzyme), another metalloprotease that releases soluble TNF and is responsible for the processing of the IL-6 receptor to thus play a central part in the wound healing process.

TIMP-4 inhibits all known MMPs, and preferentially inhibits MMP-2 and -7. TIMP4 shows 37% amino acid identity with TIMP1 and 51% homology with TIMP2 and TIMP3. TIMP4 is secreted extracellularly, predominantly in heart and brain tissue and appears to function in a tissue specific fashion with respect to extracellular matrix (ECM) homeostasis.

Further clinical studies directed to MMPs and use of MMP inhibitors in wound healing can be found in Argen et al., *Surgery,* 2006, 140 (1):72-82; Krarup, et al., *Int J Colorectal Dis,* 2013, 28:1151-1159; Bosmans et al., *BMC Gastroenterology* (2015) 15:180; Holte et al., *Brit. J. Surg.,* 2009, 96:650-54; Siemonsma et al., *Surgery,* 2002, 133 (3):268-276; Klein et al, *Eur. Surg. Res.,* 2011, 46:26-31; Moran et al., *World J. Emergency Surgery,* 2007, 2:13; Kaemmer et al., *J. Surg. Res.,* 2010, 163, e67-e72; Martens et al., *Gut,* 1991, 32, 1482-87; Fatouros et al., 1999, *Eur. J. Surg.,* 165 (10):986-92; Savage et al., 1997, 40 (8): 962-70; Oines et al., *World J Gastroenterol,* 2014 20 (35): 12637-48; Kiyama et al., *Wound Repair and Regen.,* 10 (5):308-13; Raptis et al., *Int. J. Colorectal Dis.,* 2011; de Hingh et al., *Int. J. Colorectal. Dis.,* 2002, 17:348-54; and Hayden et al., 2011, *J. Surgical Res.,* 168:315-324, the disclosures of each of which are incorporated by reference in their entirety.

Coatings

In at least some implementations, an outer surface of at least one of the cartridge body 42, the plurality of staple cavities 44, the plurality of staples 43, the sled 47, the anvil surface 33, and/or the plurality of staple drivers 48 in a surgical stapler apparatus can include a coating configured to selectively control an interaction between at least one matrix metalloproteinase (MMP) inhibitor and the outer surface of the component having the coating. Controlling the interaction between an MMP inhibitor and the outer surface of at least one component of the surgical stapler apparatus can prevent or avoid interference of the MMP inhibitor with the movement or function of stapler components within the stapler assembly which could result in the malfunctioning of the stapler apparatus.

In some implementations, the coating can include a substance that can permit or enhance adhesion of an MMP inhibitor to an outer surface (an "adhesion coating") of one or more stapler assembly components. The substance can be an absorbable substance (such as an absorbable polymer or an absorbable lubricant) which can optionally be water soluble and/or ionically charged.

Suitable absorbable polymers that can permit or enhance adhesion of an MMP inhibitor to an outer surface can include synthetic and/or non-synthetic materials. Examples of non-synthetic materials include, but are not limited to, lyophilized polysaccharide, glycoprotein, bovine pericardium, collagen, gelatin, fibrin, fibrinogen, elastin, proteoglycan, keratin, albumin, hydroxyethyl cellulose, cellulose, oxidized cellulose, oxidized regenerated cellulose (ORC), hydroxypropyl cellulose, carboxyethyl cellulose, carboxymethylcellulose, chitan, chitosan, casein, alginate, and combinations thereof. Examples of synthetic absorbable materials include, but are not limited to, poly(lactic acid) (PLA), poly(L-lactic acid) (PLLA), polycaprolactone (PCL), polyglycolic acid (PGA), poly(trimethylene carbonate) (TMC), polyethylene terephthalate (PET), polyhydroxyalkanoate (PHA), a copolymer of glycolide and ε-caprolactone (PGCL), a copolymer of glycolide and -trimethylene carbonate, poly(glycerol sebacate) (PGS), poly(dioxanone) (PDS), polyesters, poly(orthoesters), polyoxaesters, polyetheresters, polycarbonates, polyamide esters, polyanhydrides, polysaccharides, poly(ester-amides), tyrosine-based polyarylates, polyamines, tyrosine-based polyiminocarbonates, tyrosine-based polycarbonates, poly(D,L-lactide-urethane), poly(hydroxybutyrate), poly(B-hydroxybutyrate), poly(ε-caprolactone), polyethyleneglycol (PEG), poly[bis(carboxylatophenoxy)phosphazene]poly (amino acids), pseudo-poly(amino acids), absorbable polyurethanes, poly(phosphazine), polyphosphazenes, polyalkyleneoxides, polyacrylamides, polyhydroxyethylmethylacrylate, polyvinylpyrrolidone, polyvinyl alcohols, poly(caprolactone), polyacrylic acid, polyacetate, polypropylene, aliphatic polyesters, glycerols, copoly(ether-esters), polyalkylene oxalates, polyamides, poly(iminocarbonates), polyalkylene oxalates, and combinations thereof. In various embodiments, the polyester is may be selected from the group consisting of polylactides, polyglycolides, trimethylene carbonates, polydioxanones, polycaprolactones, polybutesters, and combinations thereof.

In some embodiments, the MMP inhibitor can be absorbed into or encapsulated by the synthetic or non-synthetic absorbable polymer. Further, the polymer can have one or more attractive aspects associated with it to encourage adhesion of the MMP inhibitor to areas of the staple coated with it. For example, the absorbable polymer can be porous to allow liquid containing the MMP inhibitor to pool and collect in the pores where it is retained when the liquid dries. Additionally, one or both of the MMP inhibitor or the absorbable polymer can be formulated with an ionic charge, thereby permitting them to electrostatically attract. The absorbable polymer (for example, a polyurethane) can also be formulated to attach the MMP inhibitor covalently as a pendent element to the polymer chain itself. Finally, the water solubility of the polymer itself can be manipulated to allow the polymer and the MMP inhibitor to co-mingle before water is removed from the construct leaving the drug and polymer blended.

In at least some implementations, the adhesion coating can include an absorbable lubricant. Suitable absorbable lubricants can include, for example and without limitation, any of the common tablet water insoluble lubricants such as magnesium stearate, sodium stearate, calcium stearate, powdered stearic acid, talc, paraffin, cocoa butter, graphite, lycopodium or combinations thereof. Absorbable lubricants can be fatty acid-derived, such as the stearates, for example, magnesium stearate, sodium stearate, calcium stearate and stearic acid.

The coating can also include at least one masking agent configured to prevent or at least minimize adhesion of an MMP inhibitor to the surface to which it is applied (an "anti-adhesion coating"). Suitable masking agents include, for example, non-absorbable silicone-based compounds such as silicone oil, silicone grease, silicone rubber, silicone resin, and silicone caulk. Further, non-absorbable lubricants such as silicone-based lubricants may also be employed. Examples of suitable silicone-based lubricants include, for example, polydimethylsiloxane, polyether-modified polydimethylsiloxane, polymethyl siloxanes, and the like. Other suitable masking agents can include a parlyene compound (for example, a fluorinated parlyene compound). Parlyene is the generic name for members of a unique polymer (poly-p-xylylene) series, several of which are available commercially (e.g., in the form of "Parlyene C", "Parlyene D" and Parlyene N," from Union Carbide). Parlyene compounds can be deposited by parlyene vapor deposition processes know in the art. Examples of fluorinated parlyene include parlyene HT, supplied by Specialty Coatings Systems (SCS) (Indianapolis, Ind.). Parlyene HT can be vapor deposited by means of coating apparatus supplied by SCS.

The coatings can be applied to the staples or any component of the staple cartridge in any number of ways such as, for example, as a spray or by immersion of the staples or components in the coatings. In the staple cartridge 40 shown in FIGS. 2 and 6, in some embodiments, an adhesion coating can be applied to the surface of the staple cartridge that faces a tissue surface 42, while an anti-adhesion coating can be applied to surfaces of the staple cartridge 40 that do not face a tissue surface and/or that contact the elongated channel 56 that supports the staple cartridge as shown in FIG. 2. In another embodiment, an anti-adhesion coating can be applied to both the surface of the staple cartridge that faces a tissue surface 42 and the surface of the staple cartridge 40 that is supported within the elongated channel 56 as shown in FIG. 2. The staple cavities of 44 of the staple cartridge 40 can be coated with an anti-adhesion coating to prevent the MMP inhibitor from interfering with the staple 43 exiting the staple cartridge 40 due to the staple sticking to the walls of the staple cavities.

Similarly, FIG. 7 depicts one embodiment of a staple driver 48 for use in any of the devices or methods disclosed herein. An anti-adhesion coating can be applied to one or more components of the staple driver 48 (such as one or more of the sled engagement surfaces 101 or the staple engagement surfaces 102) or the entire surface of the staple driver 48 can be coated with an anti-adhesion coating. FIG. 8 depicts one embodiment of a sled 47 for use in any of the devices or methods disclosed herein. An anti-adhesion coating can be applied to one or more components of the sled 47 (such as one or more of the central guide 104, the two left side wedges 103a, 103b, and the two right side wedges 105a, 105b) or the entire surface of the sled 47 can be coated with an anti-adhesion coating. FIG. 9 depicts a staple 43 for use in any of the devices or methods disclosed herein. An adhesion coating can be applied to surfaces of the staple that contact tissue, such as the distal tips 51 of the staple legs or the crown 53 while an anti-adhesion coating can be applied to the staple legs 49. In an alternative embodiment, an anti-adhesion coating can be applied to the distal tips 51 of the staple legs or the crown 53 while an adhesion coating can be applied to the staple legs 49.

In some embodiments, the adhesion coating and the anti-adhesion coating can be applied to the staple cartridge 40 (including all of the components of the staple cartridge) concurrently or sequentially. In one implementation, the anti-adhesion coating is applied to at least a portion of the cartridge body 42, the interior of the staple cavities 44, the staple drivers 48, the sled 47, the anvil surface 33, or the staple legs 49, while the adhesion coating is applied to at least a portion of the plurality of staples 43 (such as the distal tips 51 of the legs and/or crowns 53 of the staples 43, thereby allowing the MMP inhibitor to be delivered to the outside of tissue layers). However, in other embodiments, the adhesion coating can be applied to the staple legs 49 while the anti-adhesion coating can be applied to the distal tips 51 or crowns 53 of the staples 43 (thereby allowing the MMP inhibitor to be delivered to the inside of tissue layers).

Preferably, the anti-adhesion coating is applied to at least a portion of the cartridge body 42, the plurality of staple drivers 48, the sled 47, the anvil surface 33, and the plurality of staple cavities 44 prior to assembly of the components. In instances where the anti-adhesion coating is applied first to at least a portion of the cartridge body 42, the plurality of staple drivers 48, the sled 47, and the plurality of staple cavities 44, the staples 43 can be loaded into the plurality of staple cavities 44 prior to applying the adhesion coating. Further, in instances where the anti-adhesion coating is applied first, the adhesion coating can be applied to at least a portion of a plurality of staples 43 (such as the distal tips 51 of the legs and/or crowns 53 of the staples 43) using vapor disposition, dipping, or immersion of the staple cartridge assembly 40 into the adhesion coating.

Other disposition processes, in particular 3D printing technologies, can be used to expose only the section of the desired assemblies with either an anti-adhesion coating or an MMP inhibitor (e.g., a blended MMP-inhibitor-absorbable polymer) attachment. This would allow for selective disposition of the MMP inhibitor only on the crowns 53 and distal tips 51 of the staple legs 49, thereby allowing the MMP inhibitor to be exposed only to the desired areas for treatment rather than in areas where the MMP inhibiter is not desired (such as on or near the movable components of the surgical stapling apparatus).

Implantable Adjuncts

Various implantable adjuncts are provided for use in conjunction with surgical stapling instruments. "Adjuncts" are also referred to herein as "adjunct materials." The adjuncts can have a variety of configurations, and can be formed from various materials. In general, an adjunct can be formed from one or more of a film, a foam, an injection molded thermoplastic, a vacuum thermoformed material, a fibrous structure, and hybrids thereof. The adjunct can also include one or more biologically-derived materials and one or more drugs. Each of these materials is discussed in more detail below.

An adjunct can be formed from a foam, such as a closed-cell foam, an open-cell foam, or a sponge. An example of how such an adjunct can be fabricated is from animal derived collagen, such as porcine tendon, that can then be processed and lyophilized into a foam structure. Examples of various foam adjuncts are further described in previously mentioned U.S. Pat. No. 8,393,514 entitled "Selectively Orientable Implantable Fastener Cartridge" and filed Sep. 30, 2010.

An adjunct can also be formed from a film formed from any suitable material or combination thereof discussed below. The film can include one or more layers, each of which can have different degradation rates. Furthermore, the film can have various regions formed therein, for example, reservoirs that can releasably retain therein one or more medicants (for example, MMP inhibitors) in a number of different forms. The reservoirs having at least one medicant disposed therein can be sealed using one or more different coating layers which can include absorbable or non-absorbable polymers. The film can be formed in various ways, for example, it can be an extruded or a compression molded film.

An adjunct can also be formed from injection molded thermoplastic or a vacuum thermoformed material. Examples of various molded adjuncts are further described in U.S. Pat. Pub. No. 2013/0221065 entitled "Fastener Cartridge Comprising A Releasably Attached Tissue Thickness Compensator" and filed Feb. 8, 2013, which is hereby incorporated by reference in its entirety. The adjunct can also be a fiber-based lattice which can be a woven fabric, knitted fabric or non-woven fabric such as a melt-blown, needle-punched or thermal-constructed loose woven fabric. An adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose. Alternatively, the adjunct can include tightly interconnected fibers. The adjunct can be in a form of a sheet, tube, spiral, or any other structure that can include compliant portions and/or more rigid, reinforcement portions. The adjunct can be configured such that certain regions thereof can have more dense fibers while others have less dense fibers. The fiber density can vary in different directions along one or more dimensions of the adjunct, based on an intended application of the adjunct.

The adjunct can also be a hybrid construct, such as a laminate composite or melt-locked interconnected fiber. Examples of various hybrid construct adjuncts are further described in U.S. Pat. Pub. No. 2013/0146643 entitled "Adhesive Film Laminate" and filed Feb. 8, 2013, and in U.S. Pat. No. 7,601,118 entitled "Minimally Invasive Medical Implant And Insertion Device And Method For Using The Same" and filed Sep. 12, 2007, which are hereby incorporated by reference in their entireties.

The adjuncts can be formed from various materials. The materials can be used in various embodiments for different purposes. The materials can be selected in accordance with a desired therapy to be delivered to tissue so as to facilitate tissue in-growth. The materials described below can be used to form an adjunct in any desired combination.

The materials can include bioabsorbable and biocompatible polymers, including homopolymers and copolymers. Non-limiting examples of homopolymers and copolymers include p-dioxanone (PDO or PDS), polyglycolic acid (PGA), poly(lactic-co-glycolic acid) (PLGA), polycaprolactone (PCL), trimethylene carbonate (TMC), and polylactic acid (PLA), poly(glycolic acid-co-lactic acid) (PLA/PGA) (e.g., PLA/PGA materials used in Vicryl, Vicryl Rapide, PolySorb, and Biofix), polyurethanes (such as Elastane, Biospan, Tecoflex, Bionate, and Pellethane fibers), polyorthoesters, polyanhydrides (e.g., Gliadel and Biodel polymers), polyoxaesters, polyesteramides, and tyrosine-based polyesteramides. The copolymers can also include poly(lactic acid-co-polycaprolactone) (PLA/PCL), poly(L-lactic acid-co-polycaprolactone) (PLLA/PCL), poly(glycolic acid-co-trimethylene carbonate) (PGA/TMC) (e.g., Maxon), Poly(glycolic acid-co-caprolactone) (PCL/PGA) (e.g., Monocryl and Capgly), PDS/PGA/TMC (e.g., Biosyn), PDS/PLA, PGA/PCL/TMC/PLA (e.g., Caprosyn), and LPLA/DLPLA (e.g., Optima).

The adjuncts described herein can releasably retain therein at least one medicant that can be selected from a large number of different medicants. Medicants include, but are not limited to, any of the broad-spectrum MMP inhibitors disclosed herein.

Other medicants for use with the adjuncts include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response.

An adjunct can also include other active agents, such as active cell culture (e.g., diced autologous tissue, agents used for stem cell therapy (e.g., Biosutures and Cellerix S.L.), hemostatic agents, and tissue healing agents. Non-limiting examples of hemostatic agents can include cellulose such as oxidized Regenerated Cellulose (ORC) (e.g., Surgicel and Interceed), fibrin/thrombin (e.g., Thrombin-JMI, TachoSil, Tiseel, Floseal, Evicel, TachoComb, Vivostat, and Everest), autologous platelet plasma, gelatin (e.g., Gelfilm and Gelfoam), hyaluronic acid such as microfibers (e.g., yarns and textiles) or other structures based on hyaluronic acid, or hyaluronic acid-based hydrogels. The hemostatic agents can also include polymeric sealants such as, for example, bovine serum albumin and glutarldehyde, human serum albumin and polyethylene cross-linker, and ethylene glycol and trimethylene carbonate. The polymeric sealants can include FocalSeal surgical sealant developed by Focal Inc.

Non-limiting examples of antimicrobial agents include Ionic Silver, Aminoglycosides, Streptomycin, Polypeptides, Bacitracin, Triclosan, Tetracyclines, Doxycycline, Minocycline, Demeclocycline, Tetracycline, Oxytetracycline, Chloramphenicol, Nitrofurans, Furazolidone, Nitrofurantoin, Beta-lactams, Penicillins, Amoxicillin, Amoxicillin+, Clavulanic Acid, Azlocillin, Flucloxacillin, Ticarcillin, Piperacillin+tazobactam, Tazocin, Biopiper TZ, Zosyn, Carbapenems, Imipenem, Meropenem, Ertapenem, Doripenem, Biapenem, Panipenem/betamipron, Quinolones, Ciprofloxacin, Enoxacin, Gatifloxacin, Gemifloxacin, Levofloxacin, Lomefloxacin, Moxifloxacin, Nalidixic Acid, Norfloxacin, Sulfonamides, Mafenide, Sulfacetamide, Sulfadiazine, Silver Sulfadiazine, Sulfadimethoxine, Sulfamethizole, Sulfamethoxazole, Sulfasalazine, Sulfisoxazole, Bactrim, Prontosil, Ansamycins, Geldanamycin, Herbimycin, Fidaxomicin, Glycopeptides, Teicoplanin, Vancomycin, Telavancin, Dalbavancin, Oritavancin, Lincosamides, Clindamycin, Lincomycin, Lipopeptide, Daptomycin, Macrolides, Azithromycin, Clarithromycin, Erythromycin, Roxithromycin, Telithromycin, Spiramycin, Oxazolidinones, Linezolid, Aminoglycosides, Amikacin, Gentamicin, Kanamycin, Neomycin, Netilmicin, Tobramycin, Paromycin, Paromomycin, Cephalosporins, Ceftobiprole, Ceftolozane, Cefclidine, Flomoxef, Monobactams, Aztreonam, Colistin, and Polymyxin B.

Non-limiting examples of antifungal agents include Triclosan, Polyenes, Amphotericin B, Candicidin, Filipin, Hamycin, Natamycin, Nystatin, Rimocidin, Azoles, Imidazole, Triazole, Thiazole, Allylamines, Amorolfin, Butenafine, Naftifine, Terbinafine, Echinocandins, Anidulafungin, Caspofungin, Micafungin, Ciclopirox, and Benzoic Acid.

Non-limiting examples of antiviral agents include uncoating inhibitors such as, for example, Amantadine, Rimantadine, Pleconaril; reverse transcriptase inhibitors such as, for example, Acyclovir, Lamivudine, Antisenses, Fomivirsen, Morpholinos, Ribozymes, Rifampicin; and virucidals such as, for example, Cyanovirin-N, Griffithsin, Scytovirin, α-Lauroyl-L-arginine ethyl ester (LAE), and Ionic Silver.

Non-limiting examples of anti-inflammatory agents include non-steroidal anti-inflammatory agents (e.g., Salicylates, Aspirin, Diflunisal, Propionic Acid Derivatives, Ibuprofen, Naproxen, Fenoprofen, and Loxoprofen), acetic acid derivatives (e.g., Tolmetin, Sulindac, and Diclofenac), enolic acid derivatives (e.g., Piroxicam, Meloxicam, Droxicam, and Lornoxicam), anthranilic acid derivatives (e.g., Mefenamic Acid, Meclofenamic Acid, and Flufenamic Acid), selective COX-2 inhibitors (e.g., Celecoxib (Celebrex), Parecoxib, Rofecoxib (Vioxx), Sulfonanilides, Nimesulide, and Clonixin), immune selective anti-inflammatory derivatives, corticosteroids (e.g., Dexamethasone), and iNOS inhibitors.

Non-limiting examples of growth factors include those that are cell signaling molecules that stimulate cell growth, healing, remodeling, proliferation, and differentiation. Exemplary growth factors can be short-ranged (paracrine), long ranged (endocrine), or self-stimulating (autocrine). Further examples of the growth factors include growth hormones (e.g., a recombinant growth factor, Nutropin, Humatrope, Genotropin, Norditropin, Saizen, Omnitrope, and a biosynthetic growth factor), Epidermal Growth Factor (EGF) (e.g., inhibitors, Gefitinib, Erlotinib, Afatinib, and Cetuximab), heparin-binding EGF like growth factors (e.g., Epiregulin, Betacellulin, Amphiregulin, and Epigen), Transforming Growth Factor alpha (TGF-a), Neuroregulin 1-4, Fibroblast Growth Factors (FGFs) (e.g., FGF1-2, FGF2, FGF11-14, FGF18, FGF15/19, FGF21, FGF23, FGF7 or Keratinocyte Growth Factor (KGF), FGF10 or KGF2, and Phenytoin), Insuline-like Growth Factors (IGFs) (e.g., IGF-1, IGF-2, and Platelet Derived Growth Factor (PDGF)), Vascular Endothelial Growth Factors (VEGFs) (e.g., inhibitors, Bevacizumab, Ranibizumab, VEGF-A, VEGF-B, VEGF-C, VEGF-D and Becaplermin).

Additional non-limiting examples of the growth factors include cytokines, such as Granulocyte Macrophage Colony Stimulating Factors (GM-CSFs) (e.g., inhibitors that inhibit inflammatory responses, and GM-CSF that has been manufactured using recombinant DNA technology and via recombinant yeast-derived sources), Granulocyte Colony Stimulating Factors (G-CSFs) (e.g., Filgrastim, Lenograstim, and Neupogen), Tissue Growth Factor Beta (TGF-B), Leptin, and interleukins (ILs) (e.g., IL-1a, IL-1b, Canakinumab, IL-2, Aldesleukin, Interking, Denileukin Diftitox, IL-3, IL-6, IL-8, IL-10, IL-11, and Oprelvekin). The non-limiting examples of the growth factors further include erythropoietin (e.g., Darbepoetin, Epocept, Dynepo, Epomax, NeoRecormon, Silapo, and Retacrit).

Non-limiting examples of analgesics include Narcotics, Opioids, Morphine, Codeine, Oxycodone, Hydrocodone, Buprenorphine, Tramadol, Non-Narcotics, Paracetamol, acetaminophen, NSAIDS, and Flupirtine.

Non-limiting examples of anesthetics include local anesthetics (e.g., Lidocaine, Benzocaine, and Ropivacaine) and general anesthetic.

Non-limiting examples of anti-cancer agents include monoclonial antibodies, bevacizumab (Avastin), cellular/chemoattractants, alkylating agents (e.g., Bifunctional, Cyclophosphamide, Mechlorethamine, Chlorambucil, Melphalan, Monofunctional, Nitrosoureas and Temozolomide), anthracyclines (e.g., Daunorubicin, Doxorubicin, Epirubicin, Idarubicin, Mitoxantrone, and Valrubicin), cytoskeletal disrupters (e.g., Paclitaxel and Docetaxel), epothilone agents that limit cell division by inhibiting microtubule function, inhibitor agents that block various enzymes needed for cell division or certain cell functions, histone deacetylase inhibitors (e.g., Vorinostat and Romidepsin), topoisomerase I inhibitors (e.g., Irinotecan and Topotecan), topoisomerase II inhibitors (e.g., Etoposide, Teniposide, and Tafluposide), kinase inhibitors (e.g., Bortezomib, Erlotinib, Gefitinib, Imatinib, Vemurafenib, and Vismodegib), nucleotide analogs (e.g., Azacitidine, Azathioprine, Capecitabine, Cytarabine, Doxifluridine, Fluorouracil, 5-FU, Adrucil, Carac, Efudix, Efudex, Fluoroplex, Gemcitabine, Hydroxyurea, Mercaptopurine, and Tioguanine), peptide antibiotic agents that cleave DNA and disrupt DNA unwinding/winding (e.g., Bleomycin and Actinomycin), platinum-based anti-neoplastic agents that cross link DNA which inhibits DNA repair and/or synthesis (e.g., Carboplatin, Cisplatin, Oxaliplatin, and Eloxatin), retinoids (e.g., Tretinoin, Alitretinoin, and Bexarotene), vinca alkaloids gents that inhibit mitosis and microtubule formation (e.g., Vinblastine, Vincristine, Vindesine, Vinorelbine), anti-ileus agents, pro-motility agents, immunosuppresants (e.g., Tacrolimus), blood aspect modifier agents (e.g., Vasodilator, Viagra, and Nifedipine), 3-hydroxy-3-methyl-glutaryl-CoA (HMG CoA) reductase inhibitors (e.g., Atorvastatin), and anti-angiogenesis agents.

Exemplary medicants also include agents that passively contribute to wound healing such as, for example, nutrients, oxygen expelling agents, amino acids, collageno synthetic agents, Glutamine, Insulin, Butyrate, and Dextran. Exemplary medicants also include anti-adhesion agents, non-limiting examples of which include Hyaluronic acid/Carboxymethyl cellulose (seprafilm), Oxidized Regenerated Cellulose (Interceed), and Icodextrin 4% (Extraneal, Adept).

An adjunct in accordance with the described techniques can be associated with at least one medicant (e.g., a MMP inhibitor) in a number of different ways, so as to provide a desired effect, such as on tissue in-growth, in a desired manner. The at least one medicant can be configured to be released from the adjunct in multiple spatial and temporal patterns to trigger a desired healing process at a treatment site. The medicant can be disposed within, bonded to, incorporated within, dispersed within, or otherwise associated with the adjunct. For example, the adjunct can have one or more regions releasably retaining therein one or more different medicants. The regions can be distinct reservoirs of various sizes and shapes and retaining medicants therein in various ways, or other distinct or continuous regions within the adjuncts. In some aspects, a specific configuration of the adjunct allows it to releasably retain therein a medicant or more than one different medicant.

Regardless of the way in which the medicant is disposed within the adjunct, an effective amount of the at least one medicant can be encapsulated within a vessel, such as a pellet which can be in the form of microcapsules, microbeads, or any other vessel. The vessels can be formed from a bioabsorbable polymer.

Targeted delivery and release of at least one medicant from an adjunct can be accomplished in a number of ways which depend on various factors. In general, the at least one medicant can be released from the adjunct material as a bolus dose such that the medicant is released substantially immediately upon delivery of the adjunct material to tissue. Alternatively, the at least one medicant can be released from the adjunct over a certain duration of time, which can be minutes, hours, days, or more. A rate of the timed release and an amount of the medicant being released can depend on various factors, such as a degradation rate of a region from which the medicant is being released, a degradation rate of one or more coatings or other structures used to retains the medicant within the adjuncts, environmental conditions at a treatment site, and various other factors. In some aspects, when the adjunct has more than one medicant disposed therein, a bolus dose release of a first medicant can regulate a release of a second medicant that commences release after the first medicant is released. The adjunct can include multiple medicants, each of which can affect the release of one or more other medicants in any suitable way.

Release of at least one medicant as a bolus dose or as a timed release can occur or begin either substantially immediately upon delivery of the adjunct material to tissue, or it can be delayed until a predetermined time. The delay can depend on a structure and properties of the adjunct or one or more of its regions.

A person skilled in the art will appreciate that the present invention has application in conventional minimally-invasive and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Additional exemplary structures and components are described in U.S. application Ser. No. 15/621,565, entitled "Surgical Fastener Device for the Prevention of ECM Degradation," Ser. No. 15/621,636 entitled "Surgical Fastener Device with Broad Spectrum MMP Inhibitors," and Ser. No. 15/621,572 entitled "Surgical Stapler with Controlled Healing," which are filed on even date herewith and herein incorporated by reference in their entirety.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed:

1. A staple cartridge assembly for use with a surgical stapler, comprising:
    a cartridge body having
        a plurality of staple cavities,
        a plurality of staples, each staple being disposed within one of the plurality of staple cavities,
        a plurality of staple drivers, the plurality of staple drivers being upwardly movable to eject the plurality of staples from the plurality of staple cavities, and
        a sled longitudinally movable through the cartridge body and configured to cause upward movement of the plurality of staple drivers;
    wherein at least a first portion of an outer surface of at least one of the cartridge body, the plurality of staple cavities, the plurality of staples, and the plurality of staple drivers includes an adhesion coating configured to permit adhesion of at least one matrix metalloproteinase (MMP) inhibitor to the at least a first portion of the outer surface; and
    wherein at least a second portion of an outer surface of at least one of the cartridge body, the plurality of staple cavities, the plurality of staples, and the plurality of staple drivers includes an anti-adhesion coating configured to minimize adhesion of the at least one MMP inhibitor to the at least a second portion of the outer surface.

2. The assembly of claim 1, wherein the adhesion coating is disposed on the at least a first portion of the outer surface of the plurality of staples, and the anti-adhesion coating is disposed on the at least a second portion of the outer surface of at least one of the cartridge body, the plurality of staple drivers, and the sled.

3. The assembly of claim 1, wherein the adhesion coating is disposed on the at least a first portion of the outer surface of the plurality of staples.

4. The assembly of claim 1, wherein the anti-adhesion coating is disposed on the at least a first portion of the outer surface of at least one of the cartridge body, the plurality of staple drivers, and the sled, and wherein the anti-adhesion coating comprises at least one masking agent.

5. The assembly of claim 4, wherein the at least one masking agent is selected from the group consisting of a lubricant, parlyene, and combinations thereof.

6. The assembly of claim 5, wherein the lubricant comprises silicone.

7. The assembly of claim 1, wherein the adhesion coating is disposed on the at least a first portion of the outer surface of the plurality of staples, and wherein the coating comprises an absorbable substance.

8. The assembly of claim 7, wherein the absorbable substance is selected from the group consisting of an absorbable polymer and an absorbable lubricant.

9. The assembly of claim 8, wherein the absorbable polymer comprises polyurethane.

10. The assembly of claim 8, wherein the absorbable polymer is polymerized in the presence of the at least one MMP inhibitor, thereby resulting in an absorbable polymer/MMP inhibitor blend.

11. The assembly of claim 7, wherein the absorbable substance is water soluble.

12. The assembly of claim 7, wherein the absorbable substance is ionically charged.

13. The assembly of claim 1, wherein the adhesion coating is disposed on the at least a first portion of the outer surface of the plurality of staples, and wherein the anti-adhesion coating is disposed on the at least a second portion of the outer surface of the plurality of staples.

* * * * *